(12) United States Patent
St. Clair et al.

(10) Patent No.: US 6,265,172 B1
(45) Date of Patent: Jul. 24, 2001

(54) DIAGNOSTIC TEST AND THERAPY FOR MANGANESE SUPEROXIDE DISMUTATE (MNSOD) ASSOCIATED DISEASES

(75) Inventors: Daret K. St. Clair, Lexington, KY (US); Muneyasu Urano, Shiruoka (JP); Edward J. Kasarskis, Lexington, KY (US)

(73) Assignee: University of Kentucky, Lexington, KY (US)

( * ) Notice: Subject to any disclaimer, the term of this patent is extended or adjusted under 35 U.S.C. 154(b) by 0 days.

(21) Appl. No.: 09/499,884

(22) Filed: Feb. 8, 2000

Related U.S. Application Data

(60) Provisional application No. 60/119,188, filed on Feb. 8, 1999.

(51) Int. Cl.[7] .............................. C12Q 1/68; C12P 19/34; A61K 48/00; C07H 21/02
(52) U.S. Cl. ................ 435/6; 435/91.2; 514/44; 536/23.1; 536/24.3
(58) Field of Search ................. 435/6, 91.2; 514/44; 536/23.1, 24.3

(56) References Cited

U.S. PATENT DOCUMENTS

| | | | |
|---|---|---|---|
| 5,436,162 | * | 7/1995 | Heckl et al. ........................ 435/320.1 |
| 5,604,099 | * | 2/1997 | Erlich et al. ............................... 435/6 |
| 5,900,358 | * | 5/1999 | Ludwig et al. ........................... 435/6 |

OTHER PUBLICATIONS

Stratagene Catalog, p. 39, 1988.*
St. Clair et al, "Complementary DNA encoding human colon cancer manganese superoxide dismutase and the expression of its gene in human cells", Cancer Research 51:939–943, Feb. 1991.*
Miele et al, "SOD2 (MnSOD) does not suppress tumorigenicity or metastasis of human melanoma C8161 cells", Anticancer Res. 15:2065–2070, 1995.*
Tomblyn et al, "Distribution of MnSOD polymorphisms in sporadic ALS patients", J. Mol. Neuroscience 10:65–66, 1998.*
Fernandez–Trigo, Am J. Clin. Oncol. 18(5):454–60 Abstract Only, 1995.*
Harris et al, "Strategies for targeted gene therapy", Trends Genetics 12(10):400–405, 1996.*
Marshall, "Gene therapy's growing pains", Science 269:1050–55, 1995.*
Xu et al, "Mutations in the promoter reveal a cause for the reduced expression of human manganese superoxide dismutase gene in cancer cells" Oncogene 18:93–102, Jan. 1999.*

* cited by examiner

*Primary Examiner*—Jeffrey Fredman
(74) *Attorney, Agent, or Firm*—McDermott, Will & Emery

(57) ABSTRACT

The present invention provides a diagnostic method and a kit for detection of mutations localized within the 5' promoter region of the MnSOD gene. Such mutations are associated with diseases characterized by decreased MnSOD activity such as certain formes of cancer, and ALS. Accordingly, the diagnostic method this invention provides, comprising RFLP, direct sequencing, or PCR analysis of the region within 3 kb, the transcription initiation site will detect these disorders. This invention also provides a therapeutic method for such disorders comprising transfection of affected cells or tissues with high activity, MnSOD expression vectors, or the administration of exogenous MnSOD enzyme.

9 Claims, 10 Drawing Sheets

(1 of 10 Drawing Sheet(s) Filed in Color)

FIG. 2A

```
-3401  GGATCCTTAC AATGGAGATA GTGGGGCCAG GCATGGTGGC TCATGCCTGT
       BamH I
-3351  AATCCCAGCA CTTTGGGAGG CTGAGGCAGG CAGATCACTT CAGTCTAGGA
                                                    <NF-kB
-3301  GTTCGAGACC AGCCTGGCCA ACATGGTGAA ACCCGATCTC CACTAAAAAT
-3251  ACAAAAATTA GCCAGGCATG GTGGCACGCA CCTGTAATCC CAGCTACTCA
-3201  GGAGGCTAAG GCAGGAGAAT CACTTGAACT CAGGAGGTGG AGGTTGCAGT
-3151  GAGCCGAGAT CGCACCACTG CACTCCAGCC CAGCAACAAA GCAAGACTCT
-3101  TGATTCGGAA AGAAAAAATA AAAAAGGTT GGGGGAGACA GTGGGAGCCC
-3051  AGACTTTTGT CCTTCCCCTT GCCTAGAAGG GAGATGAGGT TGCTGGTGCT
-3001  GTGGAAGCTA TTATGGACCA TGAGGCAGCT TTGAAGACAG AAAGCCTGCA
              <AP-1
-2951  TCCTTGATGA CTCAATGGAA TTTCATCCCA ACCCAGGACT GACTGCCCCA
-2901  GATCTTTGTT ACATGAGGGA ATACACTCTT CTGTGTTTAA GAAACTGTGG
-2851  TTGGATCTGT TACTGGAATA TGAATGCAGT TAATAACTGG CTCAAAATGA
-2801  CTTCATCTCA ACCCACATTG GTTGCTTCTT CCAAACAATA TATAGGTCTG
-2751  TACTGTGGTG GGTCTCAGGA TGGCTGTGAT GTAGCCTTAG GAAGTTTATC
-2701  TATGGGAAAT CCATATTCAT GGTGTCCTGA TGTTGCAGAG GACATCCTGA
-2651  GCTGGCTGGA GTAACTTGGG ACACAGGTCA ATCGACTGTA ATCTAACTTC
-2601  TGAGGCCATT CAGTACCCTC TACAGTGGCC ACCTAAAAAA AAGGCAGCCA
-2551  GGTGTGGTGG CTCAAGCCTA TATAGATCCC AGAACTTTGG AAGGCTGAGG
-2501  TGGGAGGATC ACTTGAGCCA AGGAGTTTGA GGCCAGCCTG GGCAACATGA
-2451  AGAAACTCTG TTTCTACAAA AAATAAAAAA AATTAGCCAG GCATGGTGGT
-2401  ATGCACCTGT AGTTCCAGCT TCTTGGGAGG CTGAGGTGGA AGAATGACAT
-2351  GAGCCCAGCA AGTCGCTGCA ATCAGCCGTG ATCACGCCGC TGCACTCCAG
-2301  CCTGGGCGAC AAAAAGAAAA AGAAAACGGA GCCTGTTCAC TGGGTGTGGT
-2251  AGACAAGGTA AACTTTTCTT TACCTCCCAT ATCCCACAAC CTTGGATGTG
-2201  CTCACAGTCA TGGTAGTGTT TTGTAATGAT GTAGCTGATG ACAGGTGTGA
-2151  TGTTGGAGAT TCTTCTACCT GACTGCTGCT ATCAGTCCTA CCAGCCCCCA
-2101  ACGTTTGGTG CTTGTTCTAA AGGGCATGTC CTAGGAGTCG CTTTAAACTC
-2051  TCAAAGTATC ACTCTCTATA CAAACAAGAA GTGCAAGTAA GTAGCCTGAG
-2001  CTCAGCCTCC CAATAGGAAT ATTTCATTAT CACTAGATCA AGTCTTTCCA
-1951  TTACAATGAC TGATCTGTCT CTGAATCCTG TGGATTCATC CTTCAAAATG
-1901  CCCTTTTCTT CCAGTTCTCA TAGCTAGTGC CCTAAAAGTG ACCTGCAGTA
-1851  CCTCCTGCTG AGACGAATGT ACCAGCTTCC TAACTAGCCT GCACTCCCTT
-1801  CATCCCCCA AGTCAGTGCC AGACCACCTT GCCTGAAAAA CCACTTTCAG
-1751  TGTGTCTCAC CTCAGCAGAA ATGTTTCTCA GCTTCCAATT AACAATCACA
-1701  TCAAACCCCT GCTCTTGTCT GCGTTTTAAG GGTATCTATA GGCCGGGCGC
-1651  CGTGGCTCCT ACCTGTAATC CCAGCACTTT GGAAGGCCGA GGCGGGCAGA
                                                    <NF-kB
-1601  TCACTTGAGG TCAGGCGTTC GAGACCATCC TGACCAACAT AGTGAAACCC
-1551  CGTCTCTACC AAAAATACAA AAAAAAAAA AATAGTGGG GCGTGGAGGT
-1501  GCACGCCTGT AATTCCAGCT ACTCGGGAGG CTGAGGCAGG AGAATCGCTT
-1451  GAACCCGGGA GGCAGAGGTT CCAGTGAGCC GACATCGCGA CACAGTACTC
```

FIG. 2B

```
-1401  GAGCCTGAGC GACAGAGCGA GGCTGTGTCT CAAAAATAAA TAAATAATAA
-1351  ATTAAAAAAA TAAGAGTATC TATAACCTGG TCCCAGCCTG AATTTCCTTT
-1301  TTCACCCCAA CACGTAGCCC TAGTTACATT CTTCTGACGT CTGTAAACAA
-1251  GCCCAGCCCT TCCTGTTGTG AAGCCAAGTT CAGGTGGTTC CTCTTCGCCT
                                                    <ARE
-1201  GACTGTTTTC CCATTCCACT TACCGGAAGC CTAGTCATCC TTCGGAGGGC
-1151  TGTACAGGGG TTGCAAGAAG CAACGGAAAC GGTTCAGCAC CTGCTACCTT
-1101  CCATCATATT CTTTTCAATA AAGGGGCAAC TCCCGCCAAT GGCAGTGTAG
-1051  ATTTCCTAAC CTCTACACAT GGAAGATTCA CACCATTCAG GATTGTTGTT
-1001  TAACTGTTGA GAGAGCACTT GATACTTAAC AGCTTACTAG GCTACAAGAC
- 951  AGCGCAGGAA AGAATCCTCT GTTGTCCTTT TATGTTATCC TGAACAGTTG
- 901  GTTCACAGAG TTACTGTAAA CACACAAAAC ATGACTGCCA GGGCTTAGTA
                                       <AP-1
- 851  GTGAGGAAGG TGGGAACTAG TCCTGACTCA GTTAACTGTG CCCAGGAGAA
- 801  GCTGCTTAAC CTCAAAGGAT TTCACTATTA CTAGAATCAA TAATACCAAC
- 751  CCTAGGGGTA AAAATAAAGA TAAATGTGTG CAAATCCTGC CTGCAGTCTC
- 701  GGGCACGTCG TGGGTGTCCA AGAACTGTTC TTAGGCAGCC GGTGGGGACA
- 651  AAGTCTGTGT GCCTCCTGTC CTGGAATAGG TCCCAAGGTC GGCTTACTTG
- 601  CAAAGCAAGG GTACGGCGCA AGAGTACTGA ATACGGGTTG AAGGGCGCT
                                              >SP-1
- 551  GGCTCTACCC TCAGCTCATA GGCCGGCTGG GCGGCGCTGA CCAGCAGCTA
- 501  GGCCCCGTCT TCCCTAGGAA CGGCCACGGG GGCCCTGGGA GGGTATGAAT
- 451  GTCTTTTTGC AGTGAGGCCT CTGGACCCCG CGGCCCCCG GCAGCGCAAC
- 401  CAAAACTCAG GGGCAGGCGC CGCAGCCGCC TAGTGCAGCC AGATCCCCGC
                >SP-1
- 351  CGGCACCCTC AGGGGCGGAC CGGAGGCAGG GCCTTCGGGC CGTACCAACT
- 301  CCAAGGGGGC AGGGGCCGCC TCCCTTCGGC CGCGCGCCAC TCAAGTACGG
- 251  CAGACAGGCA GCGAGGTTGC CGAGGCCGAG GCTAGCCTGC AGCCTCCTTT
                                                >SP-1/>SP-1
- 201  CTCCCGTGCC CTGGGCGCGG GGTGTACGGC AAGCGCGGGC GGGCGGGACA
                                                    >SP-1
- 151  GGCACGCAGG GCACCCCGG GGTTGGGCGC GGCGGGCGCG GGGCGGGGCC
       <AP-2       >SP-1/>SP-1
- 101  CGCGGGGGGG GGGGCGGGGC GGCGGTGCCC TTGCGGCGCA GCTGGGGTCG
                                    >AP-2/<AP-2/>SP-1
-  51  CGGCCCTGCT CCCCGCGCTT TCTTAAGGCC CGCGGGCGGC GCAGGAGCGG
         ▶Start
-   1  CACTCGTGGC TGTGGTGGCT TCGGCAGCGG CTTCAGCAGA TCGGCGGCAT
         +1
+  50  CAGCGGTAGC ACCAGCACTA GCAGCATGTT GAGCCGGGCA GTGTGCGGGT
                                                      Exon 1
+ 100  GAGAAGAAAG GGACCCGGT CACGCGCCCA AGGGCGAAGG GGCTCGCGGC
+ 150  GGGCAGGGCC TCCGCGGCAA TGGCGACAGT GGCCGCACCG GCCTGGCGG
+ 200  GACCGGGGCA CCTGCAGGCG GTTCTCCCGG GAGTGCCCGG CGCGGCGGCT
+ 250  GGAGCGGGGA TCC    (SEQ ID NO: 11)
        BamH 1
```

DIAGNOSTIC TEST AND THERAPY FOR MANGANESE SUPEROXIDE DISMUTATE (MNSOD) ASSOCIATED DISEASES

RELATED APPLICATION

This application claims priority from Provisional Patent Application Serial No. 60/119,188 filed Feb. 8, 1999 entitled "DIAGNOSTIC TEST AND THERAPY FOR MANGANESE SUPEROXIDE DISMUTATE (mNsod)ASSOCIATE DISEASES, the entire disclosure of which is hereby incorporated by reference herein.

STATEMENT AS TO RIGHTS TO INVENTIONS MADE UNDER FEDERALLY SPONSORED RESEARCH AND DEVELOPMENT GRANTS

This invention was made with Government support under NIH grants CA 49797, CA 59835, and HL 03544, as well as grants from the Environmental Protection Agency. The Government has certain rights in this invention.

TECHNICAL FILED OF THE INVENTION

The present invention relates to a diagnostic test and diagnostic kit for disease associated with decreased superoxide dismutase transcriptional activity. The present invention also relates to method of treating such diseases by augmentation of superoxide dismutase levels in affected tissues and cells.

BACKGROUND OF THE INVENTION

Aerobic organisms possess antioxidant defense systems that modulate reactive oxygen species (ROS). The superoxide dismutase (SODs) catalyze the dismutation of superoxide radicals into hydrogen peroxide and molecular oxygen. Hydrogen peroxide is further detoxified by catalase and glutathione peroxidase (Halliwell and Gutterbridge, 1989). Three distinct SODs are found in human cells; a monodimeric cytosolic CuZnSOD (McCord and Fridovich, 1969); an extracellular homotetrameric glycosylated CuZn-SOD (ECSOD) (Marklund, 1982); and a mitochondrial matrix homotetrameric MnSOD (Weisiger and Fridovich, 1973).

Accumulating data suggest that MnSOD constitutes one of the major cellular defense mechanism against the toxic effects of agents that cause oxidative stress. It has been demonstrated that MnSOD knockout mice develop cardiomyopathy and neonatal lethality, whereas independent disruption of the genes for CuZnSOD and ECSOD isoenzymes result in viable, normal mice under nonstress conditions (reviewed in Yen and St. Clair, 1997). Furthermore, transgenic mice expressing human MnSOD in the mitochondria are protected from oxygen-induced cardiac injury (Yen et al., 1996), and ischemia-induced brain injury (Keller et al., 1998).

Numerous studies using gene transfection have demonstrated that transfection of MnSOD into tumor cells reverse the malignant phenotypes of tumor cells, suggesting that MnSOD functions to suppress tumorigenicity (reviewed in St. Clair et al., 1997). Transfection of human MnSOD cDNA into mouse fibroblasts prevents radiation-induced neoplastic transformation (St. Clair et al. 1992). Expression of the human MnSOD gene in mouse C3H10T1/2 cells enhances cellular differentiation upon treatment with 5-azacytidine (St. Clair et al. 1994). The malignant phenotype of human melanoma cells was suppressed by introduction of human chromosome 6 where the MnSOD gene is located (Trent et al. 1990) or transfection of a human MnSOD cDNA (Church et al., 1993). Overexpression of MnSOD suppressed the malignant phenotypes of human breast cancer cells (Li et al. 1995), human glioma cells (Zhong et al., 1997), and mouse epidermal cells (Amstad et al., 1997). The number of cells required to produce tumors in syngenic mice was markedly increased for the MnSOD-transfected murine fibrosarcoma cells lines (MnSOD-Fsa-II) compared to the vector-transfected control cells (St. Clair et al., 1997). The frequency of metastases was reduced in syngenic mice carrying the MnSOD transfected-FsaII cells compared to the mice bearing the control FsaII cells (Stafford et al., 1994). Furthermore the radiation dose required to control one-half of the irradiate tumor (TCD50) was greatly reduced when the MnSOD-FsaII cells were transplanted and irradiated in vivo under hypoxic conditions (Urano et al., 1995). Taken together, the evidence from these studies supports a hypothesis proposed by Oberley and Oberley (1984) that MnSOD plays an important role in the prevention of cancer development.

It has been shown that many types of human cancer cells have reduced MnSOD activity compared to their appropriate normal counterpart cells; (oberley and Buettner, 1979). The reduced level of MnSOD activity in human cancer cells is not due to a defect in the primary structure of the MnSOD protein, a change in the dosage of the MnSOD gene, or a decrease in the stability of MnSOD mRNA in tumor cells, but rather is due to defects in the expression of the gene (St. Clair and Holland, 1991).

The present inventors previously cloned and sequenced the entire human MnSOD gene, including a 0.7 kb 5' flanking region, from a genomic library obtained from normal human lung fibroblast cells. The gene is characterized by the lack of TATA or CAAT box regulatory elements and the presence of a GC-rich region containing multiple SP-1 binding sites (Wan et al., 1994).

Prior research has failed to elucidate the cause for reduced expression of MnSOD in tumor cells. The present inventors have undertaken extensive research in order to solve this problem, and have accomplished this result by discovering several highly conserved mutations in the promoter region of the MnSOD gene.

In order to elucidate the cause for the reduced expression of human MnSOD in tumor cells, the present inventors have now further sequenced the 5' flanking region of the human SOD gene and compared that to the 5' flanking region of the human MnSOD gene from several tumor cell lines. The results demonstrate three heterozygous mutations n the promoter region of the human MnSOD gene in 5 of 14 tumor cell lines examined. Significantly these mutations were conserved amongst 3 of 5 colon cancer cell lines studied. The effect of these mutations on the transcription activity of the human MnSOD promoter was also determined by means of a reporter gene constructs. These results demonstrated markedly reduced gene expression when compared to transcriptional activation of the normal, wild-type MnSOD promoter.

An object of the present invention is to provide a diagnostic kit and a diagnostic method for assaying the presence of superoxide dismutase gene mutations associated with decreased enzyme activity seen in many diseases. Specifically, this invention aims at providing a diagnostic kit and method for certain cancers associated with reduced MnSOD expression. Another object of the present invention is to provide a diagnostic test and a diagnostic kit for Amylotrophic Lateral Sclerosis, ALS, which his also associated with reduced MnSOD activity.

Another objection of the present invention is to provide a therapeutic method targeted at disease associated with decreased MnSOD activity, and more specifically targeted at cancer and ALS.

SUMMARY OF THE INVENTION

It is one of the principal objectives of the present invention to provide a diagnostic kit and a diagnostic test for the detection of MnSOD mutations associated with various diseases. It is a further object to provide such a diagnostic kit and method for cancer. The present invention provides an assay which detects mutations in the regulatory region of MnSOD gene by a variety of methods comprising RFLP analysis, in conjunction with PCR amplification or DNA hybridization (Southern Blotting) utilizing a labeled oligonucleotide probe complementary to the MnSOD promoter/enhancer.

The present invention also provides a therapeutic method directed to MnSOD associated diseases which comprises augmentation of MnSOD activity by transfection of affected cells or tissues with high activity MnSOD expression vectors, or administration of exogenous MnSOD enzyme of these sites.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 2A and 2B represent the DNA sequence of the 5' flanking region of the human MnSOD gene. The transcription initiation site is numbered as +1. Sequences are numbered relative to the transcription initiation site (+1). Potential transcription regulatory binding sites for NF-xB, ARE, AP-1, SP-1 and AP-2 are boxed. The arrow heads indicate the strand by which consensus sequences are detected.

**Significant difference in transcription activities compared to the normal promoter (p<0.01).

Figure 8:
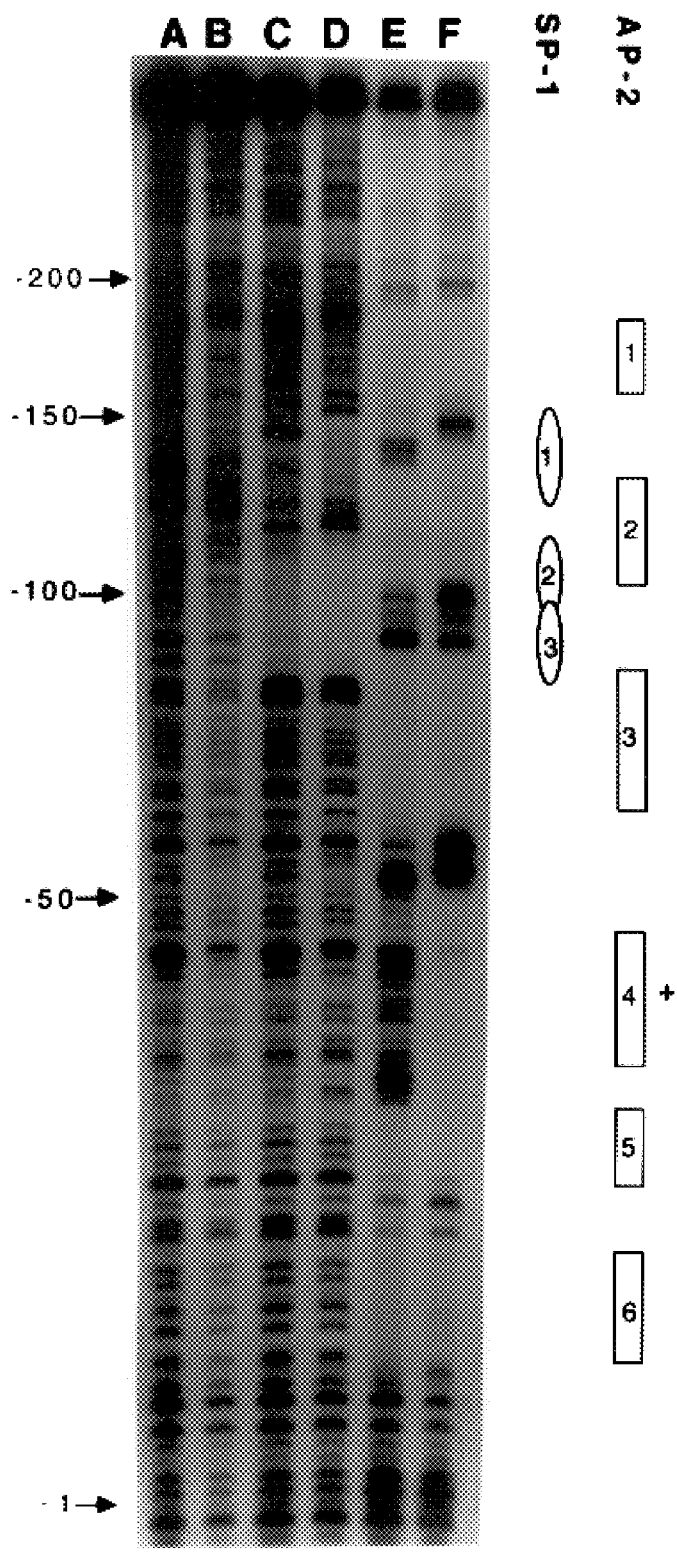

FIG. 8 is the DNAse I footprinting analysis of the human MnSOD promoter using SP-1 and AP-2 proteins. A, P7 (a normal promoter fragment), −210 to +24) no protein control; B, HT29 (the corresponding fragment from the HT29 cancer cell line) no protein control; C, P7 with SP-1 protein; D, HT29 with SP-1 protein; E, P7 with AP-2 protein; F, HT29 with AP=2 protein. The binding patters of SP-1 and AP-2 are indicated on the right. (+) represents an additional AP-2 site found only in the mutant promoter.

Figure 9:
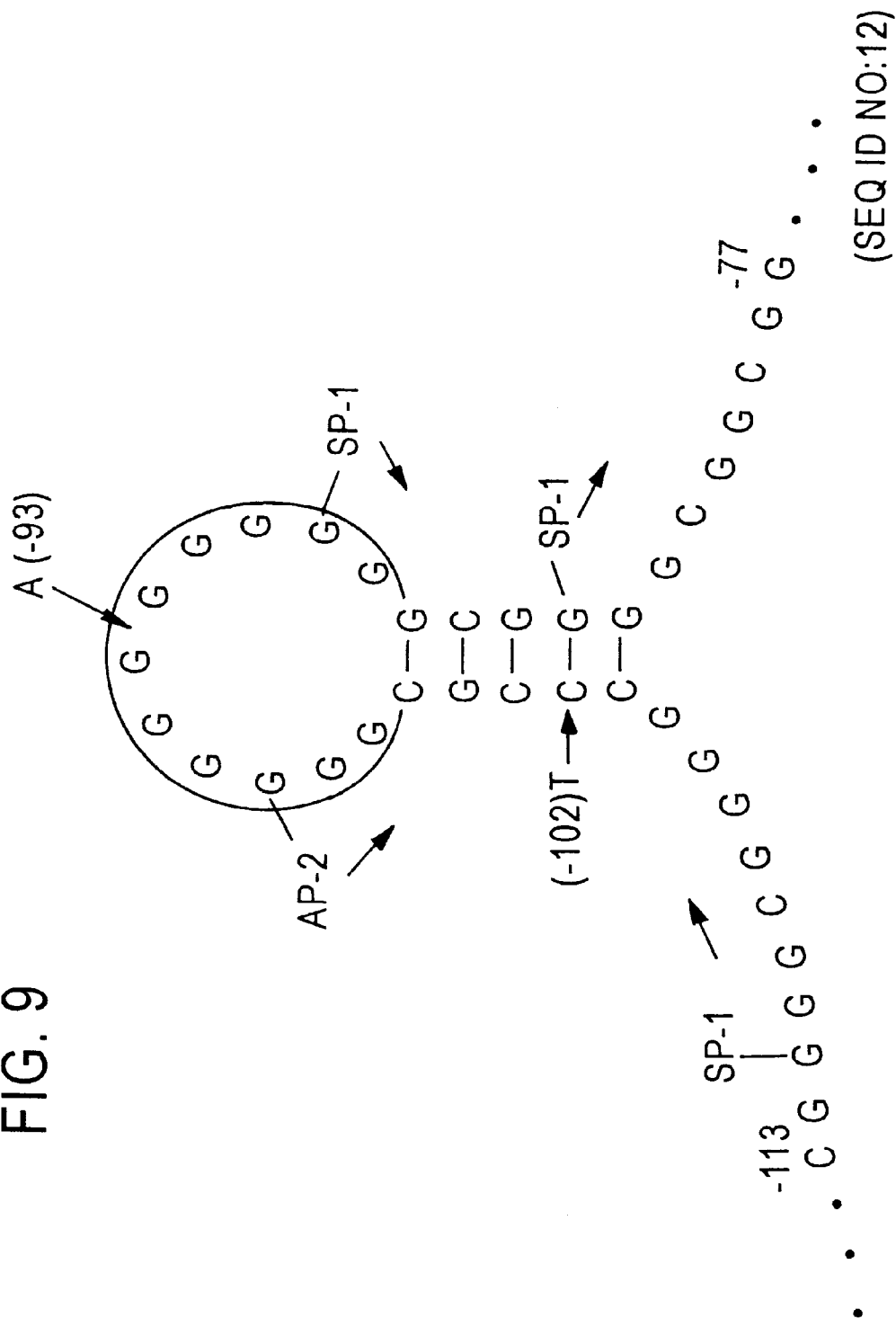

FIG. 9 Putative cruciform structure with 11-guanine unpaired loop located in the human MnSOD promoter. Three SP-1 and one AP-2 binding sites located in the DNA-looping structure are marked. Sites where mutations may disrupt the proposed structure are indicated.

DETAILED DESCRIPTION OF THE PREFERRED EMBODIMENTS

The invention may best be understood with reference to the accompanying figures wherein an illustrative embodiment is shown and in the following detailed description of the preferred embodiments.

The present invention provides a diagnostic method for detection of mutations in the MnSOD gene. This detection method comprises restriction fragment length polymorphism (RFLP) analysis or direct sequencing of the regulatory region of MnSOD following extraction of DNA isolated from cells or tissues to be assayed. This detection method may also comprise mobility shift assays which involve comparison of the electrophoretic mobility of naked DNA comprising promoter region sequences to the mobility of such a sequence after it is combined with transcription factors in-vitro, under conditions which facilitate the binding of DNA to protein. The detection method may further comprise DNAse footprinting assays, which ascertain whether the sequence in question has a transcription factor binding pattern different from the wild type sequence. Another embodiment of the present diagnostic method may also comprise isolation of the MnSOD regulatory region of the sample to be tested and subclonining such region into plasmid constructs upstream of a suitable reporter gene. Reporter gene activity of the sample construct is then compared to reporter gene transcriptional activity of a control construct driven by a wild-type promoter. Decreased reporter gene activity will indicate MnSOD promoter mutation.

The present invention further provides a therapeutic method for treating diseases associated with decreased MnSOD activity, which method comprises transfection with MnSOD.

Figure 4:
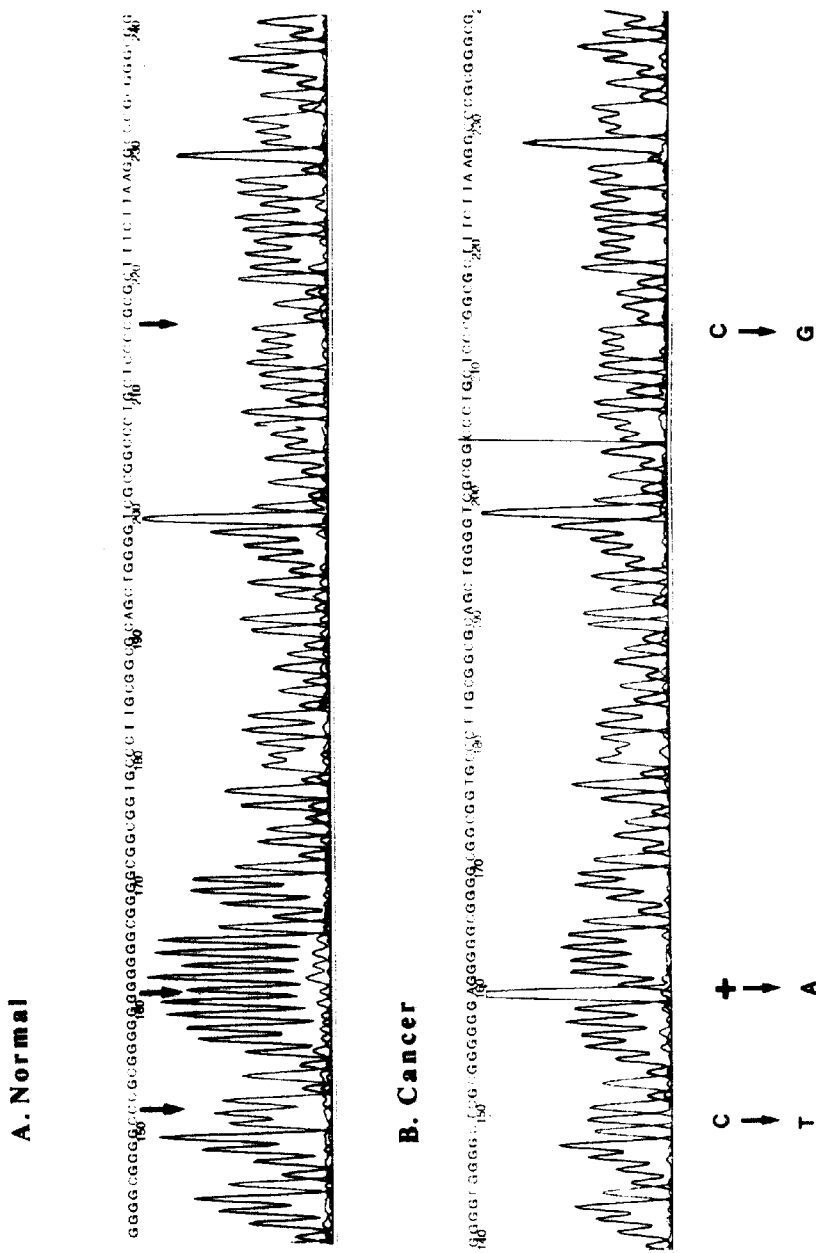
FIG. 4 is a DNA sequence analysis of the cloned PCR-4 products from the tumor cell lines. A. The wild type sequence isolated from W138. B. Mutations in 5 tumor cell lines are identified at the indicated positions. C changes to T at −102, C changes to G at −38 and A is inserted at −93.

The present inventors have identified a set of three mutations found in five of fourteen cancer cell lines tested, clustered around the GC rich region within a fragment from −210 to +24 (relative to transcription initiation site) of the MnSOD promoter (FIG. 4). The present inventors have demonstrated that these mutations affect transcription factor binding (by DNAse Footprinting assays) and transcriptional activity (by means of subcloning into a luciferase reporter gene construct). This region contains elements recognized by the transcription factors SP-1 and AP-2, suggesting that the decreased MnSOD activity associated with these cancers may be modulated by alteration of SP-1 and AP-2 binding affinities.

Isolation of Genomic NA

The present inventors isolated genomic DNA for use in the present invention assays by means of a commercially available DNA extraction kit (Stratagene), according to the manufacturer's instructions. However, any standard protocol may be used. Although cancer cell lines were utilized in this experiment (Table 1), a similar protocol, and the method which this invention teaches, is suitable for assay of cells of any origin including cells derived from patient biopsies. In brief, approximately 10" cells in 300 ml of PBS were lysed by adding pronase to a final concentration of 400 $\mu$g/ml and followed by a 30 minute incubation at 60° C. Cellular protein was removed by salt precipitation and centrifugation at 2000×g for 15 min. at 4° C. RNA was removed by incubation of the solution for 30 min. at 37° C. with RNase at a final concentration of 25 $\mu$g/ml. The DNA was recovered by ethanol precipitation, estimated spectrophotometrically and stored at 20° C.

Figure 3:
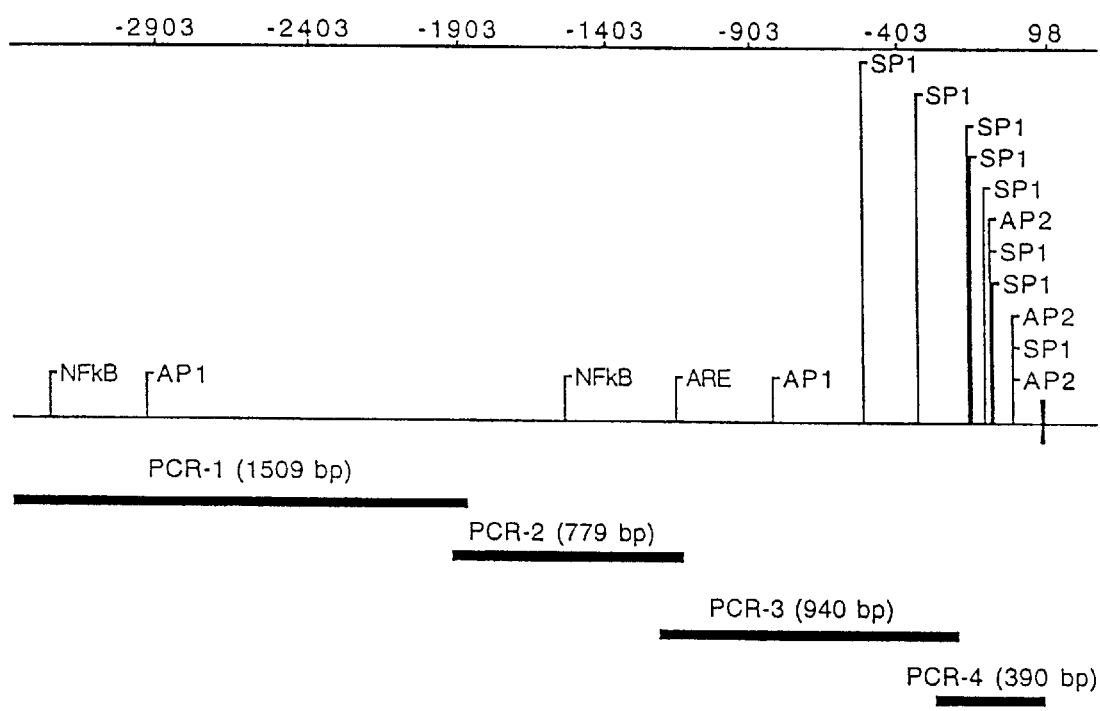
FIG. 3 is a diagram of transcription factors binding ties in the 5' flanking region of the human MnSOD gene and amplification of the 5' flanking region by polymerase chain reaction (PCR). Corresponding transcription factors binding sites for NF-xB, ARE, AP-1, AP-2, and SP-1 in the 5' flanking region are marked (top). Four PCR primer sets were designed for amplication of the 5' flanking region from the tumor cell lines (bottom).

Amplification of the 5' flanking region of the human MnSOD gene by polymerase chain reaction (PCR). A total of four PCR primer sets were designed to amplify a 3.4 kb 5' flanking region of the human MnSOD gene (FIG. 3). The oligonucleotide sequences of the primer sets were as follows:

PCR-1 (−3322 to −1813), 5'GCACATCACTTCAGTCTAGGAGT-3' (SEQ ID NO:1) and 5'-GGCTAGTTAGGAAGCTGGTAC-3' (SEQ ID NO:2);

PCR-2 (−1892 to 1093), 5'-TCCAGTTCTCATAGCTAGTGCC-3' (SEQ ID NO:3) and 5'-ATATGATGGAAGGTAGCAGGTGC-3' (SEQ ID NO:4);

PCT-3 (−1182 to −242), 5'-TTACCGGAAGCCTAGTCATCCTT-3' (SEQ ID NO:5) and 5'-TGCCTGTCTGCCGTACTTGAG-3' (SEQ ID NO:6);

PCR-4 (−321 to 70), 5'-GCCTTCGGGCCGTACCAACTCCAA-3' (SEQ ID NO:7) and 5'-CTAGTGCTGGTGCTACCGCTGATGC-3' (SEQ ID NO:8).

A highly fidelity pfu DNA polymerase (Stratagene) was used to minimize the error rate in the DNA synthesis by PCR (Flagman et al., 1994). PCR was carried out in 50 $\mu$l reaction mixture containing 20 mM Tris-CHl, pH 8.8, 2 mM MgSO04, 10 mM Kcl, 10 mM $(NH4)_2SO_4$, 0.1% Triton X-100, 1 mg/m, nuclease-free BSA, 80 $\mu$M each of dATP, dGTP, dCTP, and dTTP, 0.2 $\mu$M of each primer, 6% DMSO, 1 $\mu$g genomic DNA, and 2.5 pfu DNA polymerase. The thermal cycling settings for PCR-1, PCR-2 and PCR-3 include a 5 min initial denaturation at 95° C. followed by 35 amplification cycles (1 min denaturation at 94° C., 1 min annealing at 55 to 65° C. depending on the primer sets, and 1.5 to 3 min. extension at 75° C. depending on the length of PCR products, finished with a final extension at 72° C. for 10 min). 7-deaza-2'-dGTP (C7 dGTP, Boehringer Mannheim) was used to amplify the PCR-4 because of its GC rich nature (Innis et al, 1990). For amplification of PCR 4, the conditions were changed to, 3:1 C7 dGTP:dGTP instead of dGTP in the dNTP mixture and 160 $\mu$M dNTP: Thermal cycling settings include initial denaturation at 98° C. for 10 min, 5 cycles of 95° C. for 45 sec, and 72° C. for 1 min for primer annealing, followed by 35 cycles consisting of denaturation at 95° C. for 45 sec, annealing at 60° C. for 1 min, extension at 72° C. for 1.5 min (auto segment extension of 2 sec per cycle), and final extension at 72° C. for 10 min. The PCR products were analyzed by on a 1% agarose gel in Tris-acetate buffer with ethidium bromide staining. The products of PCR-1, PCR-2 and PCR-3 were purified from the agarose gels using a GeneClean Kit (Bio101) and the product of PCR-4 by a MC membrane (Millipore) according to the manufactures' recommendations.

Cloning

To determine the nucleotide sequence of the 5' flanking region of the human MnSOD gene, a BamIII fragment (B7) containing a 3.4 kb 5' flanking region was subcloned into M13mp18 from the 39b $\lambda$ clone. This $\lambda$ clone was derived from a genomic library prepared from human lung fibroblast cells and has been described previously (Wan et al., 1994). This $\lambda$ clone includes a complete coding region of the human MnSOD gene in addition to a 5' flanking region and a 3' flanking region (wan et al., 1994). The B7 region was mapped by restrictions endonuclease digestion. Small fragments obtained from the digested B7 were subcloned into multicloning sites of M13 mp18 and/or M13 mp 19 vectors for DNA sequencing.

To clone PCR products amplified from the 5' flanking region of human MnSOD gene, a PCR-Script Amp SK(+) vector (Stratagene) was used. The vector was derived form the pBluescript+ II SK (+) phagemid by addition of an Srf I site, which is a rare-cleavage restriction enzyme within the multiple cloning sites. Srf I recognized 8 bp oligonucleotide sequence 5'-GCCC/GGGC-3' and its cutting site is the same as Sma I (5'-CCC/GGG-3'). The use of Srf I in the ligation maintains the concentration of Sma I digested vector DNA by preventing self-ligation of the vector and allows rapid and efficient blunt-ended cloning of the PCR products amplified by pfu DNA polymerase. Screening of the PCR products was performed by the blue-white phenotype from a-complementation of lac Z gene and restriction pattern of the recombinant plasmids. For DNA sequencing, the plasmid DNA was prepared from 1.5 ml of LB culture and purified by polyethylene glycol 800 precipitation.

Sequence Analysis

Figure 1:
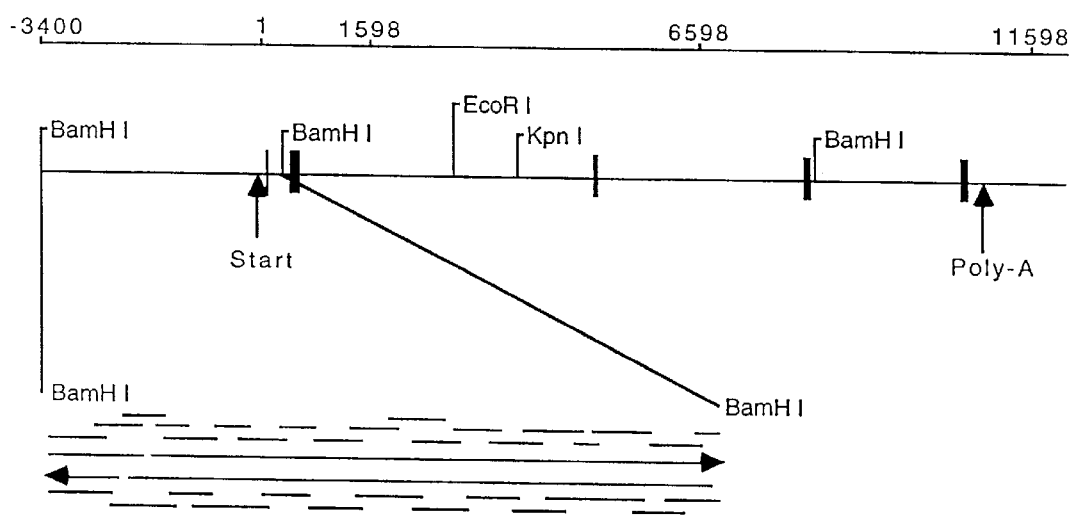
FIG. 1 is a schematic representation of the human MnSOD gene and sequencing strategy for the 5' flanking region of the gene. Physical map with restriction endonucleases BamH I, EcoR I and Kpn I is illustrated (top), showing a 3.4 kb 5' flaking region, 5 exons separated by 4 introns, and 1.36 kb 3' flanking region. The exons/coding sequences are depicted with black boxes. The transcription initiation site and poly-A are marked with arrows. A BarH I fragment containing the 5' flanking region was subcloned in M13 pm18 or M13 and mp19 vectors and sequenced in both directions (bottom).

To determine the DNA sequence in the 5' flanking region of the human MnSOD gene, single-strand DNA templates were prepared from M13 clones and the nucleotide sequences was determined on both strands by Sanger's dideoxynucleotide chain-termination method (Sanger et al., 1977) with Sequenase 2.0 (Amersham). A dITP reaction mix was used to sequence the GC rich region. Multiple overlapping fragments were sequenced at least twice in each direction (FIG. 1) and the DNA sequence was analyzed by MacVector software (Kodak) and potential transcription factor binding sites mapped (FIG. 2).

Figure 5A:
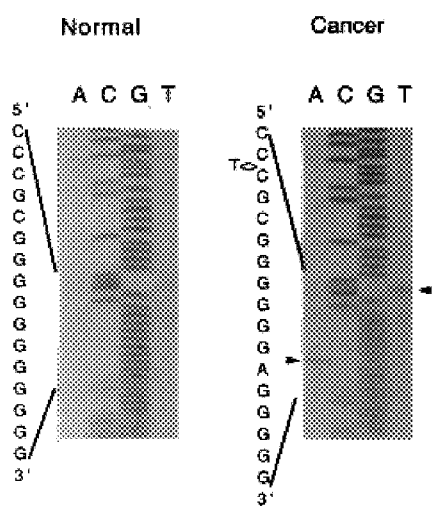
FIG. 5 is the direct sequence of PCR product for determination of a heterozygosity at each mutation site in the tumor cell lines. A. indicates C to T transition at −102 and an insertion of A at −93. B. indicates C to G transversion at −38. Arrows indicate the positions of the mutations.
Figure 5B:
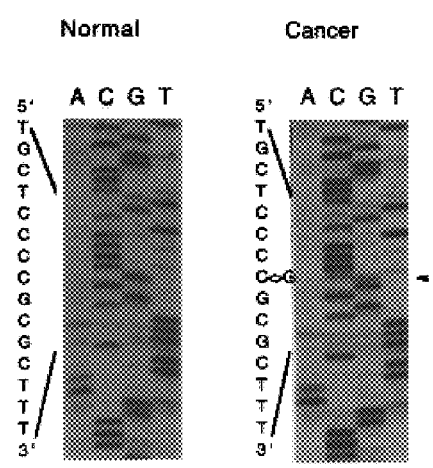

To investigate mutations in the 5' flanking region, thirty four oligonucleotides complementary to defined DNA sequences of the 5' flanking region were synthesized as DNA sequencing primers in both forward and reverse directions. DNA sequence analysis was performed by manual method (Thermo sequenase cycle sequencing kit, Amersham) and automatic sequence method (Applied biosystem) according to the manufacturers instructions (FIG. 4). Direct sequencing of PCR products was performed to confirm that the detected mutations are heterozygous in nature. 7-deaza-dGTP and 10% DMSO were used for sequencing the GC rich region (FIG. 5).

Computer analysis predicted that the mutations would alter recognition site for several restriction endoucleases (Table 2). The A insertion at −93 and the C to G transversion at −38 would create a new Mnl I (CCTCN$_7$) and an Aha I (CCSGG) restriction digestion sites respectively. However, the C to T transition at −102 would result in loss of the Apa I (GGGCCC) restriction digestion site. To verify these predictions, analysis of restriction fragment length polymorphisms (RFLP) was performed to compare restriction digestion patterns in the tumor and normal cells.

RFLP Analysis

Figure 6:
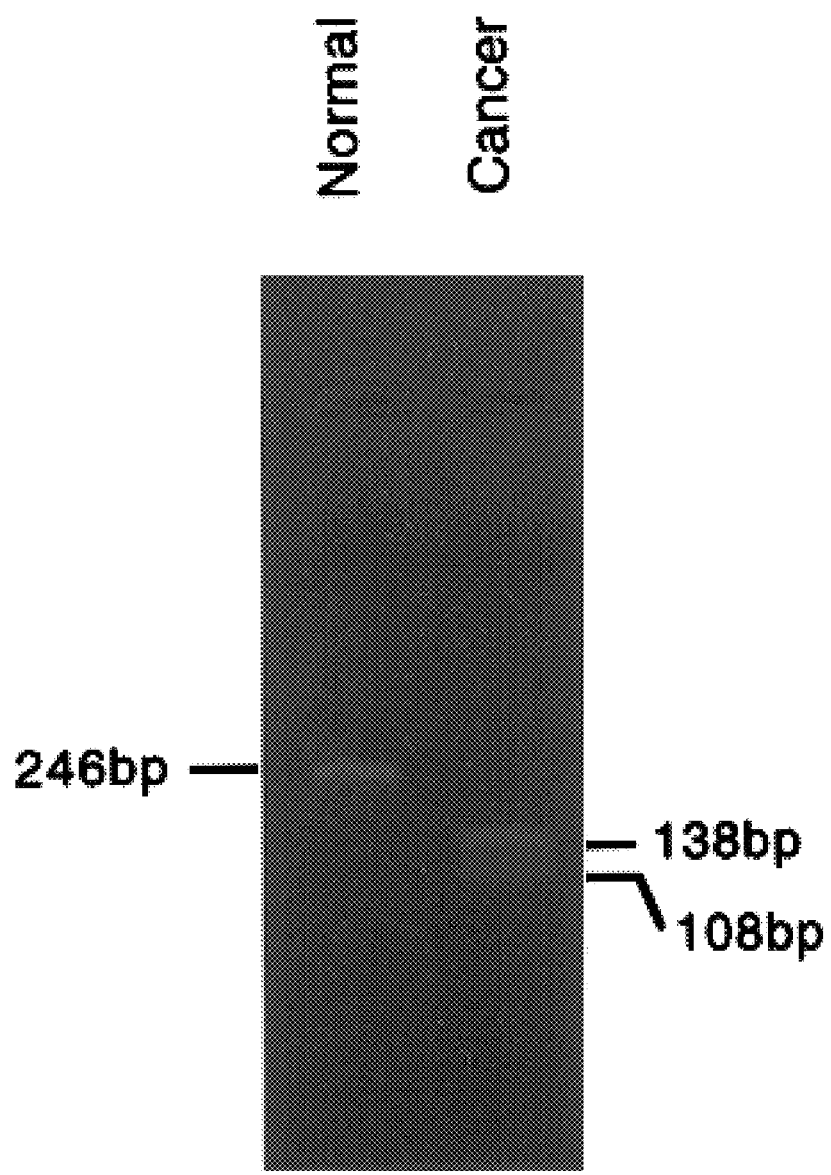
FIG. 6 is an analysis of restriction fragment length polymorphisms (RFLP) of the promoter region. The C to T mutations at −102 results in the loss of Apa I site in the tumor cell lines. The mutation at APA I site yield at 246 bp uncut fragment comparing to two smaller fragments (138 and 108 bp) from Apa I digestion.

Analysis of restriction fragment length polymorphisms was used to confirm the changes of restriction enzyme digestion sites caused by the mutations (FIG. 6). The cloned mutated and non mutated PCR products were cut with appropriate restriction enzymes, subjected to electrophoresis through a 2% agarose gel in Tris-borate buffer, stained with ethidium bromide, and photographed.

The present RFLP analysis utilized Apa I. While treatment of the normal fragment spanning −210 to +24 yielding two bands of 138 bp and 108 bp size following restriction enzyme digestion; the mutated fragment yielded only one band of 24 bp due to loss of the Apa I site (FIG. 6). It would also be feasible to perform such RFLP analysis with Aha I or Mnl I. Indeed, any mutation within the 5' promoter region would be expected to result in loss or addition of a variety of different restriction enzyme recognition sites. Thus, other mutations in the 5' promoter region could be detected by using the appropriate restriction enzyme for RFLP analysis.

Moreover, although the present RFLP analysis utilized ethidium bromide staining for detection, it is also feasible to utilize Southern blotting according to standard protocols, wherein following gel electrophoresis, the DNA is transferred to a suitable membrane such as nylon, and affixed by baking or crosslinking. Then a labeled oligonucleotide probe, complementary to a MnSOD promoter sequence would be allowed to hybridize to the adsorbed DNA fragments, and detection is accomplished by exposing the membrane to 2-ray film.

Analysis of the Promoter Activities

Figure 7A:
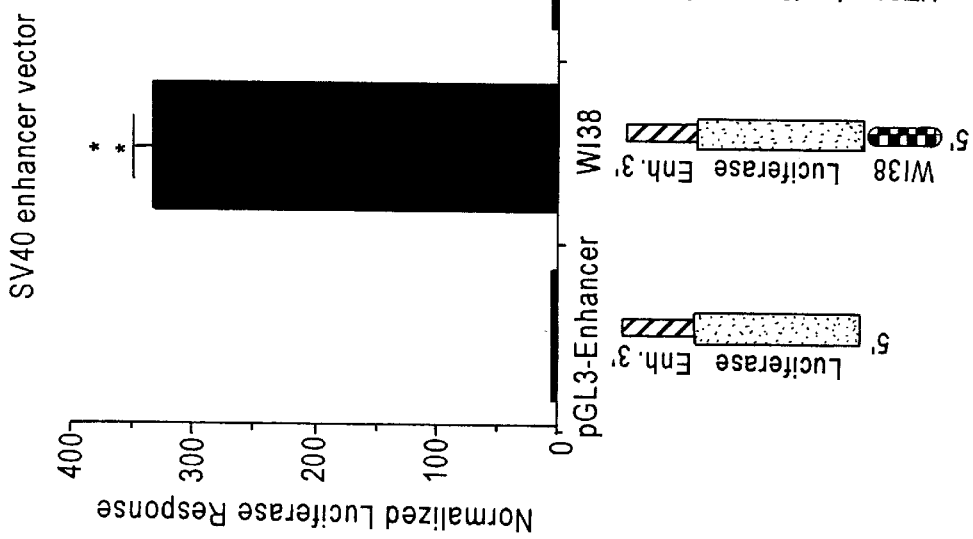
FIG. 7 demonstrates the effect of mutations in the human MnSOD promoter on gene expression. Human fibroblast cells were transfected with (A) plasmids cloned in a pGL 3 basic vector containing he human MnSOD promoter and firefly luciferase reporter gene; (B) plasmids cloned in a pGL3E vector, modified from pGL3 basic vector by addition of SV4C enhancer n 3' flanking region of the luciferase gene. Activities were normalized by a co-transfected rellina luciferase to correct for variations in transfection efficiencies.
Figure 7B:
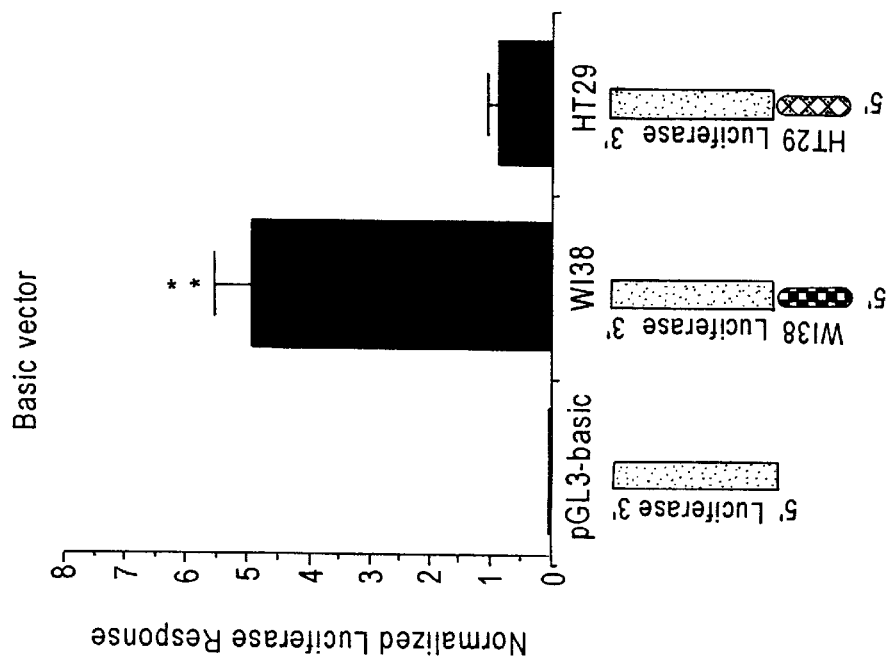

A luciferase reporter system (Promega) was used to determine changes of the promoter activity due to mutations in the human MnSOD promoter (FIG. 7). Plasmid constructs were prepared using pGL3-Basic and pGL3-SV40 enhancer vectors to subclone each promoter region upstream of the firefly luciferase reporter gene. A set of PCR primers with recognition sequences of Kpn I and Bgl II digestion on the terminals was used to amplify the promoter region −154 to +24 from the cloned PCR-4 products. The sequences of oligonucleotide primers were: 5'-CGGGGTACCACAGGCACGCAGGGCACCCCCGG GGT-3' (SEQ ID NO:9) and 5'-GGAAGATCT GCCGAAGCCACCACAGCCACGAGT-3' (SEQ ID NO:10). The PCR condition was the same as that described for the PCR-4. The PCR products were cloned into the luciferase reporter vectors within Kpn I and Bgl II sites.

The resulting plasmids were transiently transfected into the VA13 cells by the calcium phosphate mediated transfection method (Wigler et al., 1977). To control for differences in transfection efficiencies, an additional vector (Renilla luciferase, co-vector) was co-trasfeted(???) as an internal control. A mixture of 3.6 μg vector DNA and 0.4 μg co-vector DNA (10:1) was transfected into the cells (which had been plated at a density of 1×10(????) cells and incubated at 37 degrees Celsius for 16 hours prior to transfection) in a 32 mm tissue culture dish. Sixty hours after transfection, the cells were washed with PBS 3 times, harvested,and lysed by incubation with 200 μl passive lysis buffer (Promega) at room temperature for 30 min. Firefly and renilla luciferase activities were measured by a Dual-luciferases assay system using a TD-20/20 Luminometer (Promega). The mutant promoter activities were compared to the wild type promoter based on the normalized luciferase expression. Data were evaluated using a statistical analysis system (SAS Institute Inc., Cary, N.C.). Analysis of variances was performed for multiple comparison of each dependent variable. A p value <0.01 was considered to be statistically significant.

The normalized luciferase reporter activities observed by the present inventors indicates that the mutations in the prompter significantly reduced promoter activity (FIG. 7). Compared to the normal promoter activities, the mutated promoter activities decreased by more than 50% in the pGL3 constructs and 90% in the pGL3-enhancer constructs, respectively. Multiple independent transfections were performed with similar results.

Dnase I Footprinting Analysis

Dnase I Footprinting analysis was performed to detect possible changes in the binding pattern of transcription factors due to the mutations found in the promoter region of the human MnSOD gene from the tumor cell lines. Briefly, the promoter region (−210 to +24) was subcloned into a pUC18 plasmid between Kpn I and Hind III sites. A sac I/Hind III fragment was isolated from a 2% agarose gel in 0.5× Tri-borate buffer using a dialysis tubing (Gibco BRL) and dephosphorylated by an alkaline phosphates from calf intestinal (CIP, New England Biolabs). The purified fragment was labeled with λ-$^{32}$P at 5' hydroxyl terminus by T4 polynucleotide kinase (Promega_and digested with Kpn I to generate a single end-labeled fragment. Purified SP-1 and AP-2 proteins (Promega) were incubated with each labeled promoter fragment, and the DNA was partially digested by RNAse-Free DNAse. The samples were separated on a 6% polyacrylamide sequencing gel. The gel was vacuum dried and exposed to an X-ray film (Eastman Kodak Co.) at −70° C. for 16 h.

Footprints were observed at multiple binding sited for Sp-1 and AP-2 within the promoter fragment (FIG. 8). One predicted SP-1 site close to the transcription initiation site was apparently weak and could not be detected. In the normal promoter fragment (FIG. 8). One predicted SP-1 site close to the transcription initiation site was apparently weak and could not be detected. In the normal promoter fragment, five strong protected regions were observed with AP-2 protein that corresponded to sites 1, 2, 3, 5 and 6. Some AP-2 binding sites also overlap SP-1 binding sites (SP-1/AP-2). When AP-2 protein was used with the mutant promoter fragment, an additional AP-2 protected site was observed (region 4 in FIG. 8) which is consistent with the result from the computerized search. However, footprinting did not show elimination of an AP-2 binding site by the C to T transition at −102. No change was found in the SP-1 binding pattern.

Although the footprinting assay shows transcription factor binding to a given DNA sequence, it is also likely that other interactions could be observed under in-vivo conditions due to cooperative binding with other factors, and the formation of secondary and tertiary DNA structure arising out of interaction with nonadjacent sites and DNA-looping (Su et al. 1991) or DNA-bending (Ikeda) et al. 1993). It is possible that mutations in the promoter regions, which affect transcriptional activity exert this effect through alteration of promoter region secondary structures resulting from the disruption of DNA-protein as well as DNA-DNA interactions (Thomsen et al, 1994) study of secondary structure of CMV IE gene).

The present inventors propose that a putative DNA looping structure could be formed through the surrounding sequences in the human MnSOD promoter as illustrated in FIG. 9. In this case, the eleven unpaired guanosine loop might provide a specific binding domain for activation of transcription. This loop structure contains three SP-1 and AP-2 binding sites that are required for basal transcription of the gene. Deletion of this entire region has resulted in a greater than 90% decrease of transcriptional activity. Tow of the three mutations located in this region might interfere with the formation of the secondary structure, especially the C to T transition at −102 may result in an alteration of he putative loop structure. These findings suggest that other mutations which affect DNA secondary structure may be found within the MnSOD promoter region which similarly impair transcriptional activity by affecting DNA-protein or protein-protein interaction, and thus impairing treatment of polymerase. Accordingly, the present invention is not limited in scope to the three mutations detailed herein, but s also directed to the detection and treatment of other mutations, exerting similar effects, within the MnSOD promoter region.

All of the references cited herein are hereby incorporated in their entireties by reference.

While this invention has been described with an emphasis upon preferred embodiments, it will be obvious to those or ordinary skill in the art that variations of the preferred embodiments may be used and that it is intended that the invention may be practiced otherwise that as specifically described herein. Accordingly, this invention includes all modifications encompassed within the spirit and scope of the invention as defined by the following claims.

What is claimed is:

1. A method for detecting the presence of mutation within the MnSOD gene promoter region wherein the mutation is associated with cancer comprising:
   (i) carrying out restriction fragment length polymorphism analysis on a DNA test sample;
   (ii) obtaining a restriction endonuclease digestion pattern from the procedure in step (i); and
   (iii) comparing results obtained in step (ii) with restriction endonuclease digestion pattern of a wild-type MnSOD gene promoter, wherein a difference in the restriction endonuclease digestion pattern indicates the presence of at least one mutation in the MnSOD gene promoter in the DNA test sample wherein the mutation is associated with cancer.

2. The method of claim 1, wherein the MnSOD gene promoter sequence is first amplified by polymerase chain reaction technique before step (i), wherein said DNA test sample is digested with restriction enzyme which cuts at a recognition sequence within the promoter region, and wherein the resulting restriction endonuclease digestion pattern is visualized by electrophoresis, and staining with an appropriate DNA binding dye.

3. The method of claim 1, wherein the restriction endonuclease digestion pattern following restriction enzyme treatment is visualized by Southern Blot analysis wherein after gel electrophoresis, the DNA is adsorbed to an appropriate membrane and hybridized with labeled oligonucleotide probes complementary to MnSOD gene promoter enhancer sequences.

4. A method for detecting MnSOD gene promoter mutation wherein the mutation is associated with cancer comprising:
   i) sequencing a test sample DNA comprising the MnSOD gene promoter; and
   ii) comparing the sequence obtained in step (i) with a wild-type sequence, wherein a difference in the sequence indicates the presence of at least one mutation in the MnSOD gene promoter in the DNA test sample wherein the mutation is associated with cancer.

5. A method for detecting MnSOD gene promoter mutation by PCR analysis wherein the mutation is associated with cancer comprising:
   (i) making oligonucleotide primer complementary to the MnSOD gene promoter sequence containing one or more of the mutations; and
   ii) carrying out PCR procedure to amplify a sequence, wherein the presence of PCR amplified product indicates at least one mutation in the MnSOD gene promoter in the DNA wherein the mutation is associated with cancer.

6. A method for detecting MnSOD gene promoter mutation wherein the mutation is associated with cancer comprising:
   (i) admixing a test DNA sample comprising MnSOD gene promoter with at least one transcription factor comprising SP-1, AP-2 or NF-KB under conditions that facilitate DNA-protein binding;
   (ii) carrying out a DNA footprinting analysis, wherein a footprinting pattern is obtained for the test sample DNA in step (i) and;

(iii) comparing the footprinting pattern obtained in step (ii) with a footprinting pattern of a wild-type MnSOD gene promoter, wherein a difference in the footprinting pattern indicates the presence of at least one mutation in the MnSOD gene promoter in the DNA test sample wherein the mutation is associated with cancer.

7. A method for detecting MnSoD gene promoter mutation wherein the mutation is associated with cancer comprising:
   (i) admixing a test DNA sample comprising MnSOD gene promoter with at least one transcription factor comprising SP-1, AP-2 or NF-KB under conditions that facilitate DNA-protein binding;
   (ii) carrying out a DNA mobility shift analysis, wherein an electrophoretic mobility pattern is obtained for the test sample DNA in step (i) and;
   (iii) comparing the electrophoretic mobility pattern obtained in step (ii) with an electrophoretic mobility pattern of a wild-type MnSOD gene promoter, wherein a difference in the electrophoretic mobility pattern indicates the presence of at least one mutation in the MnSOD gene promoter in the DNA test sample wherein the mutation is associated with cancer.

8. A method for detecting the presence of mutation within the MnSOD gene promoter region wherein the mutation is associated with cancer comprising:
   (i) linking a reporter gene 3' to the MnSOD gene promoter region in the DNA test sample;
   (ii) assaying for expression of the reporter gene; and
   (iii) comparing results obtained in step (ii) with level of reporter gene expression obtained using wild-type MnSOD gene promoter, wherein a difference in the level of reporter gene expression indicates the presence of at least one mutation in the MnSOD gene promoter in the DNA test sample wherein the mutation is associated with cancer.

9. The method according to claim 8, wherein said reporter gene is a luciferase gene.

* * * * *

SEQUENCE LISTING

```
<160> NUMBER OF SEQ ID NOS:   12

<210> SEQ ID NO 1
<211> LENGTH: 23
<212> TYPE: DNA
<213> ORGANISM: synthetic construct

<400> SEQUENCE: 1
gcacatcact tcagtctagg agt                                           23

<210> SEQ ID NO 2
<211> LENGTH: 21
<212> TYPE: DNA
<213> ORGANISM: synthetic construct

<400> SEQUENCE: 2
ggctagttag gaagctggta c                                             21

<210> SEQ ID NO 3
<211> LENGTH: 22
<212> TYPE: DNA
<213> ORGANISM: synthetic construct

<400> SEQUENCE: 3
tccagttctc atagctagtg cc                                            22

<210> SEQ ID NO 4
<211> LENGTH: 23
<212> TYPE: DNA
<213> ORGANISM: synthetic construct

<400> SEQUENCE: 4
atatgatgga aggtagcagg tgc                                           23

<210> SEQ ID NO 5
```

-continued

```
<210> SEQ ID NO 5
<211> LENGTH: 23
<212> TYPE: DNA
<213> ORGANISM: synthetic construct

<400> SEQUENCE: 5
ttaccggaag cctagtcatc ctt                                              23

<210> SEQ ID NO 6
<211> LENGTH: 21
<212> TYPE: DNA
<213> ORGANISM: synthetic construct

<400> SEQUENCE: 6
tgcctgtctg ccgtacttga g                                                21

<210> SEQ ID NO 7
<211> LENGTH: 24
<212> TYPE: DNA
<213> ORGANISM: synthetic construct

<400> SEQUENCE: 7
gccttcgggc cgtaccaact ccaa                                             24

<210> SEQ ID NO 8
<211> LENGTH: 25
<212> TYPE: DNA
<213> ORGANISM: synthetic construct

<400> SEQUENCE: 8
ctagtgctgg tgctaccgct gatgc                                            25

<210> SEQ ID NO 9
<211> LENGTH: 35
<212> TYPE: DNA
<213> ORGANISM: synthetic construct

<400> SEQUENCE: 9
cggggtacca caggcacgca gggcaccccc gggt                                  35

<210> SEQ ID NO 10
<211> LENGTH: 33
<212> TYPE: DNA
<213> ORGANISM: synthetic construct

<400> SEQUENCE: 10
ggaagatctg ccgaagccac cacagccacg agt                                   33

<210> SEQ ID NO 11
<211> LENGTH: 3663
<212> TYPE: DNA
<213> ORGANISM: Homo sapiens

<400> SEQUENCE: 11
ggatccttac aatggagata gtggggccag gcatggtggc tcatgcctgt aatcccagca      60
ctttgggagg ctgaggcagg cagatcactt cagtctagga gttcgagacc agcctggcca     120
acatggtgaa accccatctc cactaaaaat acaaaaatta gccaggcatg gtggcacgca     180
cctgtaatcc cagctactca ggaggctaag gcaggagaat cacttgaact caggaggtgg     240
aggttgcagt gagccgagat cgcaccactg cactccagcc cagcaacaaa gcaagactct     300
tgattcggaa agaaaaaata aaaaaggtt ggggagaca gtgggagccc agactttgt       360 ccttccccctt gcctagaagg gagatgaggt tgctggtgct gtggaagcta ttatggacca     420
```

```
tgaggcagct ttgaagacag aaagcctgca tccttgatga ctcaatggaa tttcatccca    480
acccaggact gactgcccca gatctttgtt acatgaggga atacactctt ctgtgtttaa    540
gaaactgtgg ttggatctgt tactggaata tgaatgcagt taataactgg ctcaaaatga    600
cttcatctca acccacattg gttgcttctt ccaaacaata tataggtctg tactgtggtg    660
ggtctcagga tggctgtgat gtagccttag gaagtttatc tatgggaaat ccatattcat    720
ggtgtcctga tgttgcagag gacatcctga gctggctgga gtaacttggg acacaggtca    780
atcgactgta atctaacttc tgaggccatt cagtaccctc tacagtggcc acctaaaaaa    840
aaggcagcca ggtgtggtgg ctcaagccta tatagatccc agaactttgg aaggctgagg    900
tgggaggatc acttgagcca aggagtttga ggccagcctg gcaacatga agaaactctg     960 tttctacaaa aaataaaaaa aattagccag gcatggtggt atgcacctgt agttccagct   1020
tcttgggagg ctgaggtgga agaatgacat gagcccagca agtcgctgca atcagccgtg   1080
atcacgccgc tgcactccag cctgggcgac aaaagaaaa agaaacgga gcctgttcac     1140 tgggtgtggt agacaaggta aacttttctt tacctcccat atcccacaac cttggatgtg   1200
ctcacagtca tggtagtgtt ttgtaatgat gtagctgatg acaggtgtga tgttggagat   1260
tcttctacct gactgctgct atcagtccta ccagccccca acgtttggtg cttgttctaa   1320
agggcatgtc ctaggagtcg ctttaaactc tcaaagtatc actctctata caaacaagaa   1380
gtgcaagtaa gtagcctgag ctcagcctcc aataggaat atttcattat cactagatca    1440
agtctttcca ttacaatgac tgatctgtct ctgaatcctg tggattcatc cttcaaaatg   1500 ccctttctt ccagttctca tagctagtgc cctaaaagtg acctgcagta cctcctgctg    1560
agacgaatgt accagcttcc taactagcct gcactccctt catcccccca agtcagtgcc   1620
agaccacctt gcctgaaaaa ccactttcag tgtgtctcac ctcagcagaa atgtttctca   1680
gcttccaatt aacaatcaca tcaaacccct gctcttgtct gcgttttaag ggtatctata   1740
ggccgggcgc cgtggctcct acctgtaatc ccagcacttt ggaaggccga ggcgggcaga   1800
tcacttgagg tcaggcgttc gagaccatcc tgaccaacat agtgaaaccc cgtctctacc   1860
aaaaatacaa aaaaaaaaa aaatagtggg gcgtggaggt gcacgcctgt aattccagct   1920
actcgggagg ctgaggcagg agaatcgctt gaacccggga ggcagaggtt ccagtgagcc   1980
gacatcgcga cacagtactc gagcctgagc gacagagcga ggctgtgtct caaaaataaa   2040
taaataataa attaaaaaaa taagagtatc tataacctgg tcccagcctg aatttccttt   2100
ttcaccccaa cacgtagccc tagttacatt cttctgacgt ctgtaaacaa gcccagccct   2160
tcctgttgtg aagccaagtt caggtggttc ctcttcgcct gactgttttc ccattccact   2220
taccggaagc ctagtcatcc ttcggagggc tgtacagggg ttgcaagaag caacggaaac   2280
ggttcagcac ctgctacctt ccatcatatt cttttcaata aaggggcaac tcccgccaat   2340
ggcagtgtag atttcctaac ctctacacat ggaagattca caccattcag gattgttgtt   2400
taactgttga gagagcactt gatacttaac agcttactag gctacaagac agcgcaggaa   2460
agaatcctct gttgtccttt tatgttatcc tgaacagttg gttcacagag ttactgtaaa   2520
cacacaaaac atgactgcca gggcttagta gtgaggaagg tgggaactag tcctgactca   2580
gttaactgtg cccaggagaa gctgcttaac ctcaaaggat ttcactatta ctagaatcaa   2640
taataccaac cctaggggta aaataaaga taaatgtgtg caaatcctgc ctgcagtctc    2700
gggcacgtcg tgggtgtcca agaactgttc ttaggcagcc ggtgggaca aagtctgtgt    2760
```

```
                                                    -continued gcctcctgtc ctggaatagg tcccaaggtc ggcttacttg caaagcaagg gtacggcgca    2820
agagtactga atacgggttg gaagggcgct ggctctaccc tcagctcata ggccggctgg    2880
gcggcgctga ccagcagcta ggccccgtct tccctaggaa cggccacggg ggccctggga    2940
gggtatgaat gtcttttgc agtgaggcct ctggaccccg cggcccccg gcagcgcaac     3000 caaaactcag gggcaggcgc cgcagccgcc tagtgcagcc agatcccgc cggcaccctc    3060 aggggcggac cggaggcagg gccttcgggc cgtaccaact ccaaggggc aggggccgcc    3120 tccttcggc cgcgcgccac tcaagtacgg cagacaggca gcgaggttgc cgaggccgag    3180
gctagcctgc agcctccttt ctcccgtgcc ctgggcgcgg ggtgtacggc aagcgcgggc   3240
gggcgggaca ggcacgcagg gcaccccgg ggttgggcgc ggcgggcgcg gggcggggcc    3300
cgcggggggg ggggcggggc ggcggtgccc ttgcggcgca gctggggtcg cggccctgct   3360
ccccgcgctt tcttaaggcc cgcgggcggc gcaggagcgg cactcgtggc tgtggtggct   3420
tcggcagcgg cttcagcaga tcggcggcat cagcggtagc accagcacta gcagcatgtt   3480
gagccgggca gtgtgcgggt gagaagaaag gggacccggt cacgcgccca agggcgaagg   3540
ggctcgcggc gggcagggcc tccgcggcaa tggcgacagt ggccgcaccg ggcctggcgg   3600
gaccggggca cctgcaggcg gttctcccgg gagtgcccgg cgcggcggct ggagcgggga   3660
tcc                                                                 3663

<210> SEQ ID NO 12
<211> LENGTH: 38
<212> TYPE: DNA
<213> ORGANISM: Homo sapiens

<400> SEQUENCE: 12
cggggcgggg cccgcggggg ggggggcgg ggcggcgg                             38
```